United States Patent [19]
Yamazaki et al.

[11] Patent Number: 5,763,673
[45] Date of Patent: Jun. 9, 1998

[54] DIARYLHEPTANOIDE DERIVATIVE AND PHARMACEUTICAL COMPOSITION COMPRISING THE SAME

[75] Inventors: Ryuta Yamazaki; Takeshi Matsuzaki; Ritsuo Aiyama; Shusuke Hashimoto; Teruo Yokokura, all of Tokyo, Japan

[73] Assignee: Kabushiki Kaisha Yakult Honsha, Tokyo, Japan

[21] Appl. No.: 561,976

[22] Filed: Nov. 22, 1995

[30] Foreign Application Priority Data

Dec. 14, 1994 [JP] Japan ................... 6-310247

[51] Int. Cl.$^6$ ................................. C07C 49/603
[52] U.S. Cl. ................ 568/325; 514/731; 514/886
[58] Field of Search ................ 568/325; 514/731, 514/886

[56] References Cited

FOREIGN PATENT DOCUMENTS 0 241 043  10/1987  European Pat. Off.

Primary Examiner—Gary Geist
Assistant Examiner—Sreeni Padmanabhan
Attorney, Agent, or Firm—Oblon, Spivak, McClelland, Maier & Neustadt, P.C.

[57] ABSTRACT

A diarylheptanoide derivative of the following formula (1),

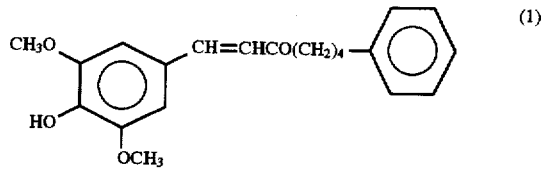

and a drug composition comprising this compound, such as a 5-lipoxygenase inhibitor, an antiinflammatory agent, and the like. The diarylheptanoide derivative (1) is effective for treating and preventing various inflammatory diseases due to its strong 5-lipoxygenase inhibiting effect.

5 Claims, 1 Drawing Sheet

DIARYLHEPTANOIDE DERIVATIVE AND PHARMACEUTICAL COMPOSITION COMPRISING THE SAME

BACKGROUND OF THE INVENTION

1. Field of the Invention

The present invention relates to a novel diarylheptanoide derivative and a pharmaceutical composition containing this compound, such as a 5-lipoxygenase inhibitor, an antiinflammatory agent, and the like.

2. Discussion of the Background

Leucotrienes exhibit strong physiological actions, such as leucocyte chemotaxis, acceleration of blood vessel permeability, and the like, and are thus known to have significant relations to inflammatory reactions. Because leucotrienes are synthesized from arachidonic acid derived from cell membrane by the action of 5-lipoxygenase, various studies are ongoing about the compounds capable of inhibiting the activity of the 5-lipoxygenase, thereby inhibiting the synthesis of leucotrienes which cause inflammatory diseases.

Conventionally, diarylheptanoide derivatives, typified by Yakuchinone-A and Yakuchinone-B having the following chemical formulas (2) and (3), which are isolated from *Alpinia offcinarum*, a plant belonging to the species of ginger, are known as a drug exhibiting a 5-lipoxygenase inhibiting activity.

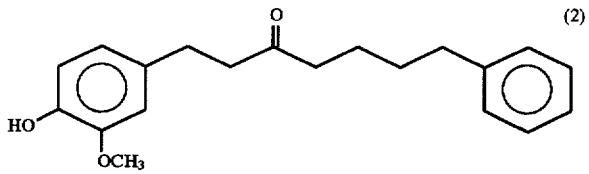
(2)

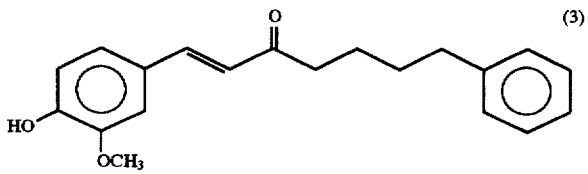
(3)

However, because the 5-lipoxygenase inhibiting activity of these diarylheptanoide derivatives is not necessarily sufficient, a drug exhibiting a stronger 5-lipoxygenase inhibiting activity, that is, a drug exhibiting a stronger antiinflammatory effect, has been desired.

In view of this situation, the inventors of the present invention have undertaken extensive studies and have found that a specific diarylheptanoide derivative possesses a strong 5-lipoxygenase inhibiting and antiinflammatory activity and is useful as a drug. This finding has led to the completion of the present invention.

SUMMARY OF THE INVENTION

Accordingly, an object of the present invention is to provide a diarylheptanoide derivative having the following chemical formula.

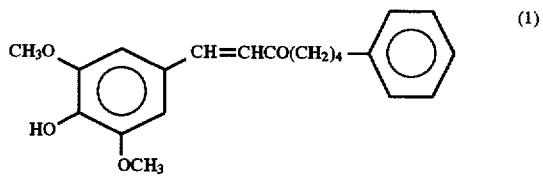
(1)

Another object of the present invention is to provide a 5-lipoxygenase inhibitor and an antiinflammatory agent comprising the diarylheptanoide derivative (1) as an effective component.

Still another object of the present invention is to provide use of the diarylheptanoide derivative (1) as a drug.

A further object of the present invention is to provide a drug composition comprising the diarylheptanoide derivative (1) and a pharmaceutically acceptable carrier.

A still further object of the present invention is to provide a method of treating an inflammatory disease comprising administering an effective amount of the diarylheptanoide derivative (1) to a patient suffering from the inflammatory disease.

Other objects, features and advantages of the invention will hereinafter become more readily apparent from the following description.

DETAILED DESCRIPTION OF THE PREFERRED EMBODIMENTS

Figure 1:
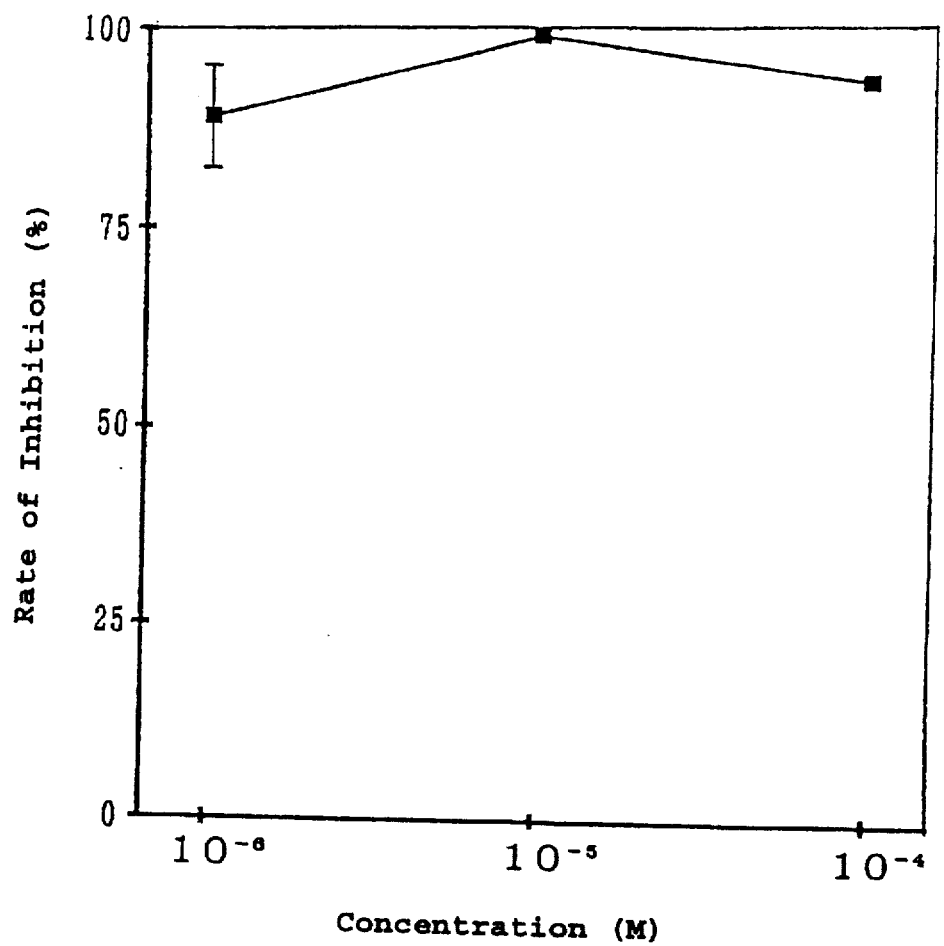
FIG. 1 is a drawing showing the 5-lipoxygenase inhibiting effect in the example of the present invention.

The diarylheptanoide derivative (1) of the present invention has stereoisomers, E-isomer and Z-isomer. Both the E-isomer and the Z-isomer, as well as mixtures of these isomers, are included in the present invention. Furthermore, the diarylheptanoide derivative (1) of the present invention has hydrates and solvates. These hydrates and solvates are also included in the present invention.

The diarylheptanoide derivative (1) can be prepared, for example, by reacting 1-phenyl-5-hexanone (4) and 3,5-dimethoxy-4-hydroxy benzaldehyde (5) in the presence of a base or a mixture of a base and an acid according to the following chemical reaction formula (1).

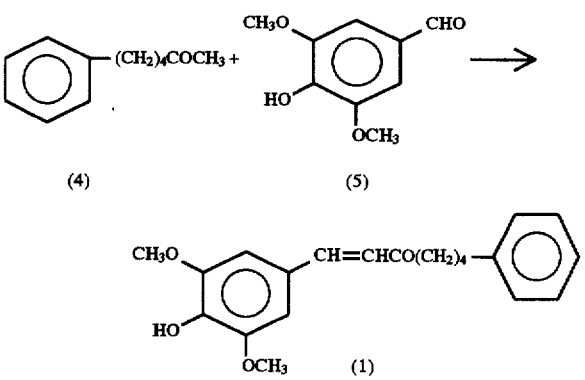

In the above process, potassium hydroxide alcholate or sodium hydroxide alcholate are used as the base. As the mixture of a base and an acid, a mixture, for example, of pyrrolidine and acetic acid, can be used. The reaction is preferably carried out in the presence of a solvent, such as ethanol, benzene, tetrahydrofuran, or ether, or a mixture of these solvents, at room temperature to −78°C.

The antiinflammatory agent containing the diarylheptanoide derivative (1) thus prepared is useful for preventing or treating various inflammatory diseases, such as chronic rheumatism arthritis, atopic dermatitis, and the like, due to its effect of inhibiting 5-lipoxygenase.

The drug of the present invention can be administered to patients for the treatment of these diseases via any route; per oral, per rectum, parenterally, or by local administration. The dose may be appropriately determined according to the age, the degree of disease, the weight, and the like. Usually, a daily dose, as the diarylheptanoide derivative (1), is selected from the range of 0.1–200 mg/kg, preferably 1–100 mg/kg, and may be dosed once a day or may be dosed in several portions.

The drug of the present invention is usually used as a composition comprising a pharmaceutically acceptable carrier such as, for example, an excipient and other additives commonly used in drugs. Examples of the additives include solid additives, such as lactose, kaolin, sucrose, crystalline cellulose, corn starch, talc, agar, pectin, stearic acid, magnesium stearate, lecithin, and sodium chloride, liquid additives, such as glycerine, peanut oil, polyvinyl pyrrolidone, olive oil, ethanol, benzyl alcohol, propylene glycol, and water.

The drug may be of any form, such as a solid preparation (e.g. tablet, powder, granule, capsule, suppository, troches, etc.) or a liquid preparation (e.g. syrup, emulsion, soft gelatin capsule, cream, gel, paste, spray, injection, etc.). No toxicity was found in the drug of the present invention.

Other features of the invention will become apparent in the course of the following description of the exemplary embodiments which are given for illustration of the invention and are not intended to be limiting thereof.

EXAMPLES

Example 1

Preparation of 1-(3,5-dimethoxy-4-hydroxyphenyl)-7-phenyl-1-heptene-3-one (1)

1.7 ml of acetic acid was added dropwise to a solution of pyrrolidine (25 ml) in benzene (100 ml) under cooling with ice. The mixture was stirred for 30 minutes. After the temperature was raised to room temperature, a solution of 5.29 g of 1-phenyl-5-hexanone in 50 ml of benzene was added and the mixture was stirred for 30 minutes. A solution of 3.6 g of 3,5-dimethoxy-4-benzaldehyde in 100 ml of tetrahydrofuran was added dropwise, followed by stirring for 48 hours before terminating the reaction. 200 ml of 1 N hydrochloric acid solution was added to the reaction mixture to separate the benzene layer. The benzene layer was washed with water, dried with saturated sodium hydrogen sulfite, and filtered. The solvent was evaporated from the filtrate under reduced pressure to obtain an oily mixture. This oily mixture was purified by a silica gel column chromatography using a 2:1 mixture of hexane and ethyl acetate as an eluant, followed by recrystallization from a 1:1 mixture of hexane and ethyl acetate to obtain 4.37 g of colorless needle crystals of compound (1). The results of analysis of this compound are as follows.

IR $v_{max}$ (cm$^{-1}$): 3481, 2941, 2922, 1653, 1624, 1605, 1591, 1514, 1456, 1246, 1214, 1114

1H-NMR δ (CDCl$_3$): 1.26(m, 4H), 2.67(m, 4H), 3.93 (s, 6H, OCH$_3$×2), 5.81(br.s, 1H, OH), 6.60(d, 1H, J=16 Hz), 6.79(s, 2H), 7.19(m, 3H), 7.27(m, 2H), 7.45(d, 1H, J=16Hz)

Test Example 1

5-Lipoxygenase inhibiting activity

A sample of 5-lipoxygenase was prepared from basophilic leukemia cells of rat (RBL-1). First, the RBL-1 was cultured in an MEM medium (manufactured by Nissui Pharmaceutical Co.) containing 0.0292% of L-glutamine and 10% of FCS under conditions of 5% $CO_2$ and at 37° C. for 3 days. After culture, the cells were collected by centrifuge (1000 rpm, 10 min., 4° C.) and washed twice with Dulbeccol's PBS (−) (manufactured by Nissui Pharmaceutical Co.). The cells were suspended in 50 ml of Tris-HCl buffer (pH 7.4) at a concentration of 7.5×10$^7$ cells/ml. The cell suspension was ultrasonically treated in an ice bath and centrifuged (1300 rpm, 30 min., 4° C.) to obtain a 5- lipoxygenase sample as supernatant. This 5-lipoxygenase sample exhibited a protein activity of 20–160 ng/min/mg.

76 μl of 50 mM Tris-HCl buffer (pH 7.4) containing 2.56 mM of $CaCl_2$ and 2.56 mM of ATP and 20 μl of 5-lipoxygenase sample prepared above were added to 2μl of a solution containing a prescribed amount of the diarylheptanoide derivative (1) prepared in Example 1 in DSMO. The mixture was incubated at 37° C. After 15 minutes, the reaction was terminated with the addition of 200 μl of a 145:55:0.1 mixture of acetonitrile, methanol, and acetic acid. The reaction mixture was centrifuged (1300 rpm, 30 min., 40° C.). The amount of 5-HETE in the supernatant was measured by HPLC (column: Nova-pak 5C18; eluant: a 60:40 acetonitrile:0.05 M $KH_2PO_4$ solution with 5 mM trihexyl bromide added; flow rate: 0.8 ml/min.; wavelength: 235 nm). The amount of 5-HETE produced was calculated from the peak area of the 5-HETE. This procedure was repeated twice to determine the 5-lipoxygenase inhibiting activity of the diarylheptanoide derivative (1) from the average production amount of 5-HETE. The results are shown in FIG. 1, which indicates the 5-lipoxygenase inhibiting activity of the diarylheptanoide derivative (1).

Test Example 2

Ear edema induction test with TPA (12-O-tetradecanoylphorbol-13-acetate)

The diarylheptanoide derivative (1) prepared in Example 1 and, as a comparative compound, 1-(3,4-dihydroxyphenyl-7-phenyl-1-heptene-3-one with the chemical formula (6) below, which is reported as a Yakuchinone derivative exhibiting the most strong 5-lipoxygenase inhibiting action, were applied to both sides of right ear of ICR male mouse (age: 6 weeks), each in an amount of 0.5 mg/ear, together with 10 μl of an acetone solution of TPA (40 μg/ml).

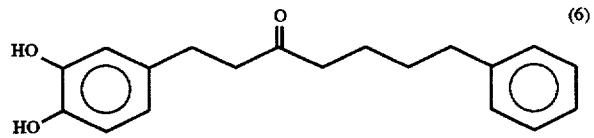

(6)

Four hours after the application of TPA, the center of right and left ears was cut out with a punch with a diameter of 6.5 mm to measure the weights. The rate of edematization of ears was calculated according to the following formula:

$$\text{The rate of edematization (\%)} = \frac{\text{(Weight of right edematized ear)} - \text{(Weight of left normal ear)}}{\text{(Weight of left normal ear)}} \times 100$$

The rate of edema enlargement inhibition was determined taking the rate of edematization of the control group to which no compound was applied as 100. The results are shown in Table 1.

TABLE 1

| Sample | Dose (mg/ear) | Rate of edematization (%) | Rate of inhibition (%) |
| --- | --- | --- | --- |
| Compound (1) | 0.5 | 6.3 | 96.1 |
| Comparative compound (6) | 0.5 | 24.9 | 84.5 |
| Control group | — | 161.1 | — |

As clear from Table 1, the diarylheptanoide derivative (1) of the present invention has a strong effect for inhibiting TPA induced edematization in ears. The effect is stronger than that of the comparative compound 1-(3,4-dihydroxyphenyl)-7-phenyl-1-heptene-3-one (6). No toxicity was exhibited by the compound (1) of the present invention when 5 mg/ear, a concentration 10 times of the effective concentration, was applied to ears of mice.

As illustrated above, the diarylheptanoide derivative (1) of the present invention is effective for treating and preventing various inflammatory diseases due to its strong 5-lipoxygenase inhibiting effect.

Obviously, numerous modifications and variations of the present invention are possible in light of the above teachings. It is therefore to be understood that, within the scope of the appended claims, the invention may be practiced otherwise than as specifically described herein.

What is claimed is:

1. A diarylheptanoide derivative having the following chemical formula (1),

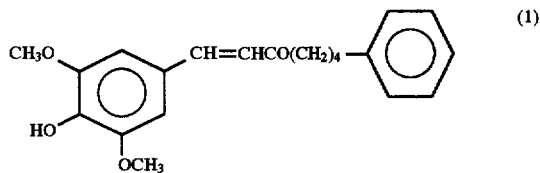

(1)

2. A 5-lipoxygenase inhibitor comprising the diarylheptanoide derivative (1) defined in claim 1 as an effective component.

3. An antiinflammatory agent comprising the diarylheptanoide derivative (1) defined in claim 1 as an effective component.

4. A pharmaceutical composition comprising a diarylheptanoide derivative having the following chemical formula (1),

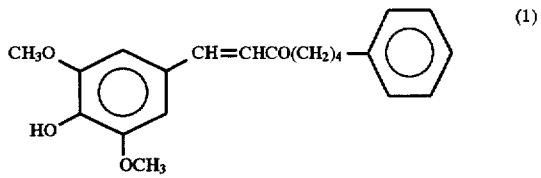

(1)

and a pharmaceutically acceptable carrier.

5. A method of treating an inflammatory disease comprising administering an effective amount of the diarylheptanoide derivative of the following formula (1),

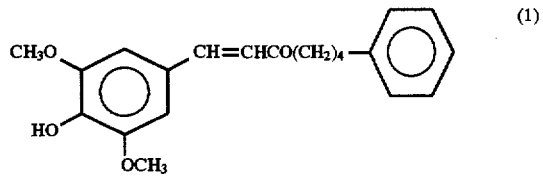

(1)

to a patient suffering from the inflammatory disease.

* * * * *